United States Patent
Kent et al.

(12)

(10) Patent No.: US 6,548,087 B1
(45) Date of Patent: Apr. 15, 2003

(54) NUTRITIONAL SUPPLEMENT

(76) Inventors: Frances B. Kent, E-Gal Corporation, 600 Central Ave., Highland Park, IL (US) 60035; Jason C. Birnholz, The E-Gal Corporation, 600 Central Ave., Highland Park, IL (US) 60035

( * ) Notice: Subject to any disclaimer, the term of this patent is extended or adjusted under 35 U.S.C. 154(b) by 0 days.

(21) Appl. No.: 09/611,971

(22) Filed: Jul. 6, 2000

Related U.S. Application Data

(60) Provisional application No. 60/143,162, filed on Jul. 12, 1999.

(51) Int. Cl.⁷ ................................................ A61K 35/78
(52) U.S. Cl. ........................ 424/728; 424/643; 514/561; 514/178; 514/355; 514/356
(58) Field of Search ............................. 424/195.1, 725, 424/728, 643; 514/561, 178, 355, 356

(56) References Cited

U.S. PATENT DOCUMENTS 4,835,147 A * 5/1989 Roberts ...................... 514/178
5,523,087 A * 6/1996 Shiyankevich ........... 424/195.1
6,007,824 A * 12/1999 Duckett et al. .......... 424/195.1

FOREIGN PATENT DOCUMENTS

WO          9951252      * 10/1999

OTHER PUBLICATIONS

Dombrowski et al. "Verapamil . . . incidentaloma" Ann. Pharmacother. (29, No. 10, 999– 1001, 1995).*

* cited by examiner

Primary Examiner—Jean C. Witz
(74) Attorney, Agent, or Firm—Charles E. Temko

(57) ABSTRACT

A dietary supplement for improvement of sexual dysfunction without resulting in undesirable side effects which occasionally accompany the use of prescription medicaments used for this purpose. The composition comprises the amino acid L-Arginine in cooperation with smaller amounts of Panax Ginseng, Niacin Amide, DHEA and Zinc.

3 Claims, No Drawings

NUTRITIONAL SUPPLEMENT

This application claims the benefit of provisional application No. 60/143,162 filed Jul. 12, 1999.

This invention relates generally to the treatment of sexual dysfunction, and more particularly to an improved orally administered nutritional supplement based on new research which will provide a physiological effect comparable to that obtained by the use of far more expensive prescription type drugs, and when used in proper dosage, is relatively free of known side effects, accompanying the use of such prescription drugs.

Sexual arousal is mediated principally by the short lived, neurotransmitter nitric oxide (NO). Central stimulation (i.e. erotic images) and direct genital stimulation indicates a metabolic sequence of steps in specialized genital nerve cells with enzymatic cleavage of a nitrogen group from the amino acid L-Arginine and replacing hydrogen atoms of that group with oxygen. These steps require the enzyme nitric oxide synthetase (NOS). No is a molecular messenger that diffuses rapidly from nerve cell endings to smooth muscle cells in small blood vessels where it activates the enzyme guanylate cyclase, forming guanosine monophosphae (GMP) that relaxes smooth muscle. In the penis and clitoris, the effect of the NO-GMP pathway is to trap blood in the venous sinusoids leading to erection and other features of sexual arousal. Sildenifil citrate (viagra®) inhibits a specific phosphodiesterase enzyme that degrades the GMP, in effect, amplifying and prolonging the effects of NO production. This mechanism of sexual arousal has been studied thoroughly and is well known in the art. (See references.)

Sexual arousal cannot occur unless NO is also produced, which in turn requires the presence of a source molecule. Several well known drugs, such as tri-nitroglycerin used for angina, function as nitric oxide donors. The principal source for nitric oxide in the body is L-Arginine which is synthesized in the body (from tryptophan) and hence not regarded as an "essential" amino acid. The synthesis rate is variable and either synthesis or storage of arginine decreases with age. Arginine is supplemented from dietary sources, which are mainly red meats and also some grains. There is one report of treating erectile dysfunction with oral L-Arginine.

The NO-GMP pathway is an integral part of uterine biochemistry and appears to be activated by the hormone progesterone. Factors that increase NO production, diminish or abolish contractions. One of the factors that seems to be important in the initiation of labor is inhibition of the NO effect. There is a potential use of NO donor agents in preventing premature labor. Painful menses (dysmenorrhea) is associated with forceful and prolonged contractions, and an additional, potential use of a NO donor agent is in relieving painful menstrual cramps.

DETAILED DESCRIPTION OF THE DISCLOSED EMBODIMENT

The principal ingredient is L-Arginine, 500 mg/capsule, as a NO source. There is also 25 mg of Panax Ginseng, which is now considered to be a nitric oxide donor, and 20 mg of Niacin, which appears to facilitate production of NOS, although this has not yet been studied, nor is it to be found in the medical literature It is of interest that Niacin overdoses result in facial flushing, visual disturbances, headache, and diarrhea, which are also sides effects of Viagra®. There is also DHEA (dehydroepiandrosterone) which has been shown to increase libido and performance in daily use, probably through a central effect, since it does not modify serum testosterone level. Serum DHEA levels are low in men with erectile dysfunction. The use of high dose orally administered DHEA alone for treatment of sexual dysfunction is known in the art from U.S. Pat. No. 4,835,147. (Dehydoepiandrosterone therapy for amelioration of prostate hyperthrophy and sexual dysfunction.) There is also added Zinc (7.5 mg as the gluconate sale), since this mineral is depleted by its incorporation into semen. The supplement is intended for use by both men and women. The Arginine-Nitric Oxide pathway pertains to arousal and sexual function equally in both sexes. Like Sildenifil citrate, the supplement will facilitate and enhance arousal, but is not intended to initiate arousal or alter mood. There are no known safety issues with the specified amounts of ingredients or with the disclosed dose. For ease of administration, the supplement is prepared from finely powdered materials, mechanically mixing the same without water or other solvent, and directly filling gel capsules. The following example is illustrative.

EXAMPLE 1

| | |
|---|---|
| L-Arginine | 500 mg |
| DHEA | 25 TO 50 mg. |
| Panax Ginseng | 25 mg |
| Niacin Amide | 20 mg |
| Zinc (as gluconate salt) | 7.5 mg |

The above amounts are conveniently inserted into a single gel capsule. For male and female use, two capsules are ingested daily, in the morning, and an additional two capsules are ingested approximately thirty minutes before relations. Obviously, each response will vary on an individual basis, and depending upon the cause and severity of sexual dysfunction. Therefore, sixteen of twenty adults without known sexual dysfunction reported a subjective improvement in libido and sexual performance beginning and continuing after three weeks of daily supplementation. Five subjects had an increase in nocturnal erections measured with impedance plethysmography (REFRICAN) after one month of oral supplemental use.

Reference:

1. Burnett A L. The role of nitric oxide in the physiology of erection. Biol Reprod 1995;52:485–489.
2. Morales A, Heaton J P W,. Johnston B, Adams M. Oral and topical treatment of erectile dysfunction. Urol Clin North Am 1995;22:879–886.
3. Zorgniotti A W, Lizza A F, Effect of large doses of nitric oxide precursor L-Arginine on erectile failure, Int J Imp Res. 1994; 6:33–34.
4. Okawa T, Syal A S, Vedernikov Y P, et al. The effects of nitric oxide on the contractility of isolated uterine and aortic rings from pregnant rats. Am J Obstet Gynecol 1998; 179:721–726.
5. Yallampalli C, Izumi H, Byam-Smith M S, Garfield RE. An L-Arginine nitric oxide-cyclic guanosine monophosphate system exists in the uterus and inhibits contractility during pregnancy. AM J Obstet Gynecol 1993; 170:175–185.
6. Goldstein I, Lue T F, Padma-Nathan H, Rosen R C, Steers W D, Wicker P A. Oral sildenafil in the treatment of erectile dysfunction. N Eng J Med 1998; 338:1397–1404.

I wish it to be understood that I do not consider the, invention to be limited to the precise details of treatment set forth in the specification, for obvious modifications will occur to those skilled in the art to which the invention pertains.

We claim:

1. A dietary supplement consisting of: L-Arginine, Panax Ginseng, Niacin Amide, DHEA, and Zinc.

2. A dietary supplement consisting of the following parts by weight:

| | |
|---|---|
| L-Arginine | 550 mg |
| Panax Ginseng | 25 mg |
| Niacin Amide | 20 mg |
| DHEA | 75–50 mg |
| Zinc (as gluconate salt) | 7.5 mg |

3. The method of stimulating sexual arousal comprising the steps of:

a) preparation of a composition consisting of:

| | |
|---|---|
| L-Arginine | 550 mg |
| Panax Ginseng | 25 mg |
| Niacin Amide | 20 mg |
| DHEA | 25–50 mg |
| Zinc (as gluconate salt) | 7.5 mg | b) ingesting daily and approximately thirty minutes before relations, the composition in a range of one to two times the amount indicated.

* * * * *